(12) United States Patent
Houston et al.

(10) Patent No.: US 7,968,036 B2
(45) Date of Patent: Jun. 28, 2011

(54) METHOD FOR INTRODUCING AN INTERNAL HELICAL FORMATION INTO A FLEXIBLE TUBULAR MATERIAL

(75) Inventors: John Graeme Houston, Perth (GB); Peter Arno Stonebridge, Perth (GB); John Bruce Cameron Dick, Coupar Angus (GB); Robert Gordon Hood, Longforgan (GB); Allana Johnstone, Kippendavie Meadows (GB); Christophe Emmanuel Sarran, Glencarse (GB); Craig McLeod Duff, Dundee (GB)

(73) Assignee: Tayside Flow Technologies Limited, Dundee (GB)

( * ) Notice: Subject to any disclaimer, the term of this patent is extended or adjusted under 35 U.S.C. 154(b) by 197 days.

(21) Appl. No.: 12/082,157

(22) Filed: Apr. 10, 2008

(65) Prior Publication Data

US 2008/0319536 A1     Dec. 25, 2008

Related U.S. Application Data

(62) Division of application No. 10/300,298, filed on Nov. 20, 2002, now abandoned.

(30) Foreign Application Priority Data

Nov. 20, 2001   (GB) ................... 0127869.6

(51) Int. Cl.
 *B29C 57/00* (2006.01)
 *B29C 59/02* (2006.01)
 *B31F 1/20* (2006.01)
 *A61F 2/06* (2006.01)

(52) U.S. Cl. ........ 264/295; 264/229; 264/231; 264/257; 264/259; 264/271.1; 264/284; 264/286; 264/287; 264/294; 264/296; 264/319; 264/320; 264/324; 264/330; 264/331.11; 264/507; 623/1.22; 623/1.28; 623/1.29; 623/1.32; 623/1.44; 623/1.45

(58) Field of Classification Search ................. 264/319, 264/320, 330, 331.11, 331.14, 229, 231, 264/257, 259, 271.1, 284, 286, 287, 294, 264/296, 324, 507; 623/1.22, 1.28, 1.29, 623/1.32, 1.44, 1.45
See application file for complete search history.

(56) References Cited

U.S. PATENT DOCUMENTS

| 2,713,885 | A | * | 7/1955 | Mckinley | 156/143 |
|---|---|---|---|---|---|
| 3,197,853 | A | | 8/1965 | Felix | 29/450 |
| 4,604,762 | A | | 8/1986 | Robinson | 623/1.44 |
| 4,629,458 | A | | 12/1986 | Pinchuk | 623/1 |
| 5,108,417 | A | | 4/1992 | Sawyer | 623/1.22 |
| 5,152,785 | A | * | 10/1992 | Kowligi et al. | 623/2.26 |
| 5,238,642 | A | | 8/1993 | Benquet et al. | 264/284 |

(Continued)

FOREIGN PATENT DOCUMENTS

AT     134543     8/1933

(Continued)

*Primary Examiner* — Christina Johnson
*Assistant Examiner* — Atul Khare
(74) *Attorney, Agent, or Firm* — Renner, Kenner, Greive, Bobak, Taylor & Weber

(57) ABSTRACT

There is disclosed a method for introducing a helical formation (11) into a flexible tubular material (12). The material (12) is supported together with a surrounding helical former (13) so as to deform the material (12) to have a helical indentation (11) corresponding to the shape of the former (13). The material (12) is then set in that configuration and the former (13) is removed.

19 Claims, 2 Drawing Sheets

U.S. PATENT DOCUMENTS

| | | | | |
|---|---|---|---|---|
| 5,344,425 | A | 9/1994 | Sawyer | 606/198 |
| 5,619,878 | A | 4/1997 | Grosjean et al. | 72/56 |
| 5,653,745 | A | 8/1997 | Trescony et al. | 623/1.29 |
| 5,756,035 | A | 5/1998 | Underwood et al. | 264/295 |
| 5,938,587 | A * | 8/1999 | Taylor et al. | 600/139 |
| 5,992,465 | A | 11/1999 | Jansen | 138/37 |
| 6,053,939 | A * | 4/2000 | Okuda et al. | 623/1.43 |
| 6,071,305 | A * | 6/2000 | Brown et al. | 623/1.43 |
| 6,099,557 | A | 8/2000 | Schmitt | 623/1.1 |
| 6,161,399 | A * | 12/2000 | Jayaraman | 66/170 |
| 6,187,054 | B1 * | 2/2001 | Colone et al. | 128/898 |
| 6,203,735 | B1 * | 3/2001 | Edwin et al. | 264/127 |
| 6,338,739 | B1 | 1/2002 | Datta et al. | 623/1.15 |
| 6,416,540 | B1 | 7/2002 | Mathur | 623/1.15 |
| 6,776,194 | B2 | 8/2004 | Houston et al. | 138/39 |
| 7,185,677 | B2 | 3/2007 | Houston et al. | 138/39 |
| 2003/0120257 | A1 | 6/2003 | Houston et al. | 604/523 |
| 2003/0180488 | A1 * | 9/2003 | Lim et al. | 428/35.2 |
| 2003/0225453 | A1 | 12/2003 | Murch | 623/1.21 |

FOREIGN PATENT DOCUMENTS

| | | |
|---|---|---|
| EP | 0 255 408 A1 | 2/1988 |
| EP | 1 036 551 A2 | 9/2000 |
| EP | 1 127 557 A1 | 8/2001 |
| EP | 1 254 645 B1 | 11/2002 |
| EP | 1 314 406 B1 | 5/2003 |
| FR | 2 523 361 | 9/1983 |
| FR | 2 657 945 A3 | 8/1991 |
| GB | 862795 * | 3/1961 |
| GB | 933172 | 8/1963 |
| GB | 2 382 776 A | 6/2003 |
| SU | 1697787 A1 | 12/1991 |
| WO | WO 90/12550 | 11/1990 |
| WO | WO 98/23228 A1 | 6/1998 |
| WO | WO 98/41168 A1 | 9/1998 |
| WO | WO 99/55256 | 11/1999 |
| WO | WO 00/38591 | 7/2000 |
| WO | WO 0038591 A2 * | 7/2000 |
| WO | WO 01/89419 | 11/2001 |
| WO | WO 2004/047908 A2 | 6/2004 |

* cited by examiner

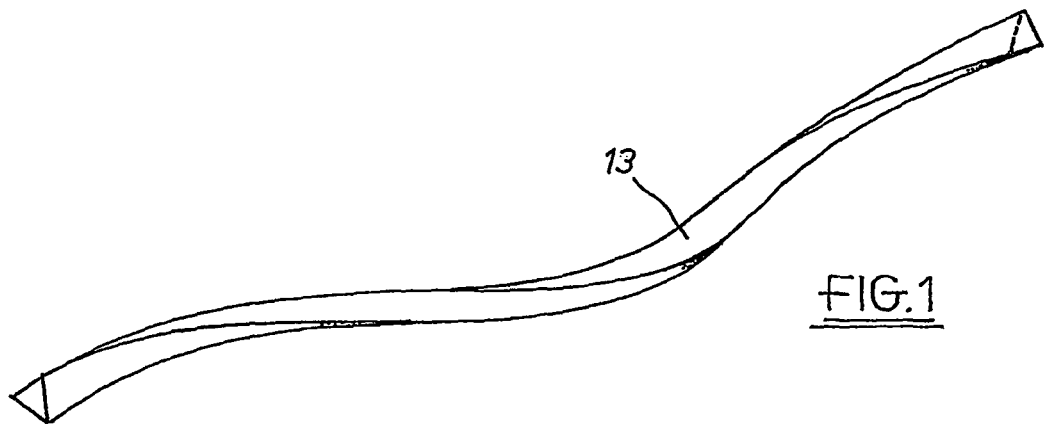
FIG. 1
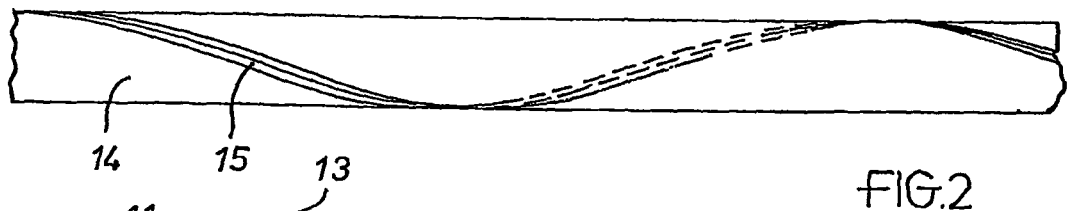
FIG. 2
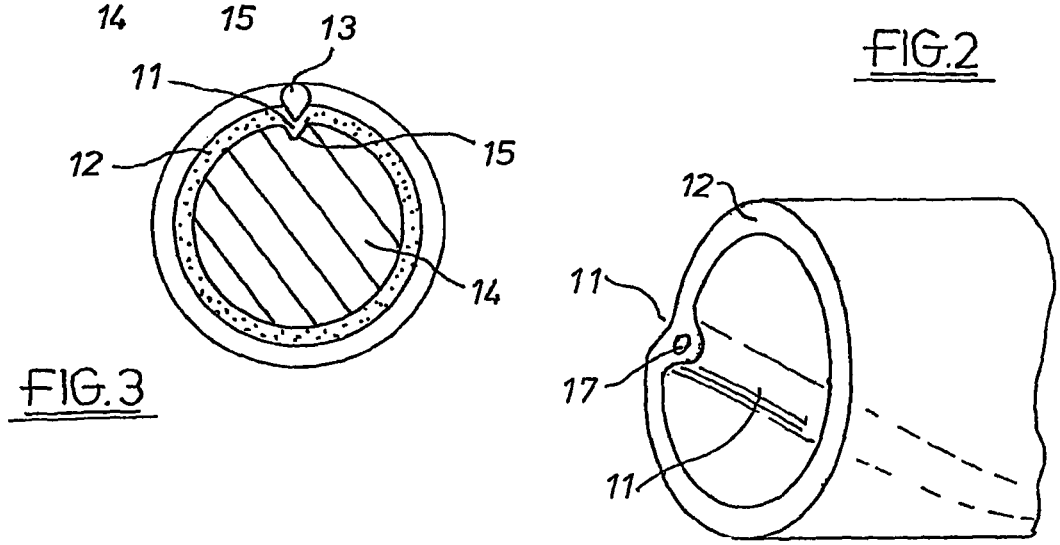
FIG. 3
FIG. 5
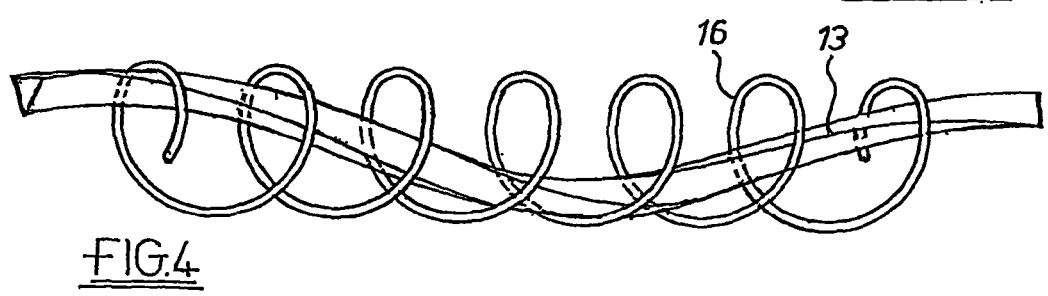
FIG. 4

METHOD FOR INTRODUCING AN INTERNAL HELICAL FORMATION INTO A FLEXIBLE TUBULAR MATERIAL

CROSS REFERENCE TO RELATED APPLICATION

This application is a division of U.S. patent application Ser. No. 10/300,298 filed Nov. 20, 2002 now abandoned, which is incorporated herein by reference.

FIELD OF THE INVENTION

This invention relates to a method for introducing an internal helical formation into a flexible tubular member.

DESCRIPTION OF THE PRIOR ART

WO 00/38591 discloses the concept of helical formations in tubes for the purpose of improving in certain desirable respects, the flow of fluid through them.

In particular, blood flow tubing, such as vascular grafts, can benefit markedly from internal helical formations such as ridges or grooves, which, if appropriately configured having regard to the tube dimensions and the density, viscosity and flow rate of blood therethrough, can eliminate turbulent flow and dead regions which can lead to plaque formation, which, in turn, can lead to reduced flow capacity or thromboses.

SUMMARY OF THE INVENTION

However, one of the problems with implementing this is how to form the helical formation within the tube.

In accordance with a first aspect of the invention, there is provided a method for introducing an internal helical formation into a flexible tubular material, the method comprising supporting the material on a mandrel having a groove, placing a helical former corresponding to the groove around the material so as to deform the material to have an internal helical formation corresponding to the shape of the groove, setting the material in that configuration, and removing the former and the mandrel.

In accordance with a second aspect of the present invention, there is provided a tube for a human or animal body, the tube comprising a flexible tubular material, a side wall of the tube being deformed to form a helical formation in the internal surface of the side wall of the tube.

The term "helical" as used herein covers the mathematical definition of helical and any combination of the mathematical definitions of helical and spiral.

The material is effectively clamped between the mandrel and the former.

In one example, the material may be supported in a surrounding structure together with the former—the surrounding structure may comprise a cage such as a wire helix.

Whilst, as compared to the multi-start helical formulations proposed in WO 00/38591, the method of the present invention is particularly adapted to the introduction of a single start helical formation, it is found that such a formation is remarkably effective. Of course the method of the invention could readily be adapted to the introduction of multi-start helical formations, if required, either by having a multiple former arrangement or by using a single former repeatedly with an appropriate angular shift.

Typically, the tubular material may be thermoplastic or thermosetting, and the material may be set by heat setting. Typically, the material is of a woven or knitted structure in polyester. However, other materials such as PTFE and polyurethane, can be spun or extruded to the required shape.

For vascular prostheses, it may be important to provide a degree of extensibility, so that the prosthesis may be under some tension between the anastomoses. Any heat setting operation should leave the tubular material, therefore, still elastically extensible.

In order to provide the correct helix angle in a prosthesis in its tensional configuration, the material may be pre-tensioned for the introduction of the formation.

The material, after the formation has been set into it, may be coated with a bio-compatible dispersion, e.g. with polyurethane. Typically, the former creates a groove in the external wide wall of the tubular material, and the dispersion is introduced into the groove in the external side wall. This helps to ensure that the internal formation maintains its shape.

Preferably, the dispersion is pressed into the material but typically does not penetrate the material to the inside surface. Preferably, the penetration is at least 50%, but less than 100%, and most preferably, 80% to 90% penetration.

A strand of a second material, which may have a different modulus of elasticity to the tubular material, may be introduced into and secured in the external helical formation after the setting operation. The strand may be a monofilament or a multifilament strand. The strand may be secured by a subsequent coating.

The effect of the strand will be an extension of the finished prosthesis for implant, to introduce a modular formation to the prosthesis, mimicking natural blood vessels.

BRIEF DESCRIPTION OF THE DRAWINGS

Method of introducing an internal helical formation into a flexible tubular material in accordance with the invention will now be described with respect to the accompanying drawings, in which:

FIG. 1 is a view of a helical former for use in the method;

FIG. 2 is a view of a helically grooved mandrel for use in one method according to the invention;

FIG. 3 is a cross-section through the mandrel of FIG. 2, with the material and former in place;

FIG. 4 is a view of a cage, with former in place, in a second method according to the invention;

FIG. 5 is a cross-section of a helically deformed tube with a filament insert;

DESCRIPTION OF THE PREFERRED EMBODIMENTS

FIG. 1 shows a helical former 13. FIG. 2 shows a mandrel 14 having a helical groove 15 formed in the external surface of the mandrel 14. The helical shape and cross-sectional shape of the former 13 corresponds to the helical shape and cross-sectional shape of the groove 15.

Figure 9:
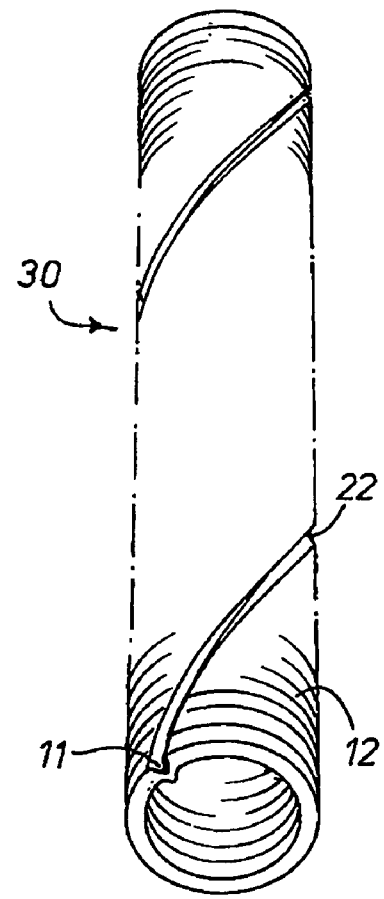
FIG. 9 is a perspective view of a vascular graft manufactured using the method of the invention.

FIG. 3 illustrates a method of using the former 13 and the mandrel 14 to form an internal helical formation 11 in a tubular material 12 to form a vascular graft 30 (see FIG. 9). The tubular material 12 is supported on the mandrel 14 with the groove 15 corresponding to the configuration of the helical former 13. The material 12 is effectively clamped between the mandrel 14 and the former 13, and forced into the groove 15 by the former 13. For example, the mandrel 14 may be stainless steel and the former 13 may be PTFE.

Initially, the material 12 is placed on a straight (non-grooved) mandrel (not shown) and a thread is wound around the outside of the material 12. The ends of the material 12 are then pushed together so that the material 12 is concertinaed. The friction between the material 12 and the mandrel maintains the material in the concertinaed configuration. The material 12 is then heat set at 95° C. to 105° C. for 3 to 4 hours. The thread may be removed before or after heat setting.

After this first heat set, the concertinaed material 12 is placed on to the mandrel 14 and the former 13 wound around the material, so that is engages with groove 15 in the mandrel 13 and the material 12 is clamped in the groove 15 between the mandrel 14 and the former 13. The material 12 is then heat set again at approximately 95° C. to 105° C. to set a helical formation 11 corresponding to the groove 15 and former 13.

Typically, before applying the former, tension is applied to the material 12 and this tension is maintained while the former 13 is wound around the material 12 and mandrel 14. Hence, during the second heat set, the material 12 is heat set with pretension. This allows a degree of flexibility but helps prevent further extension of the material 12, which would change the helix angle of the helical formation 11. It also minimises the risk of graft movement or longitudinal extension post surgery.

Figure 6:
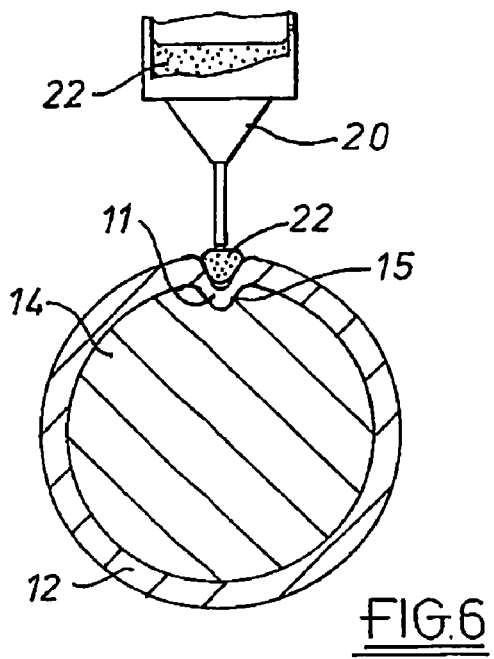
FIG. 6 is a cross-sectional view of a tube after forming of the helical formation and having a polyurethane dispersion applied.
Figure 7:
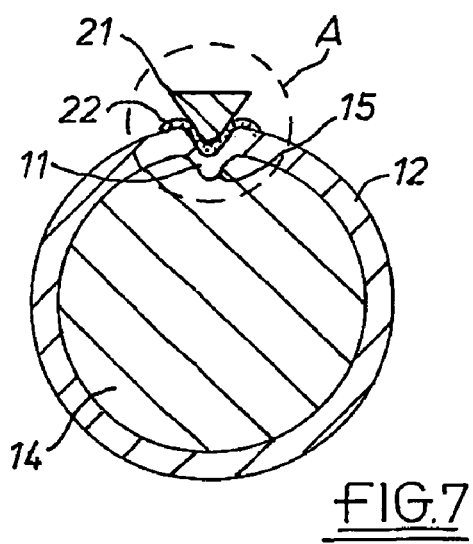
FIG. 7 is a cross-section view of the tube of FIG. 6 with a former being used to press the polyurethane dispersion into the material of the tube.
Figure 8:
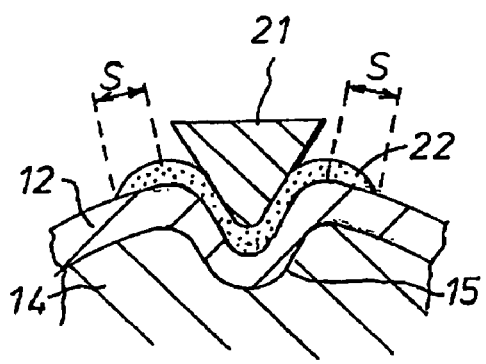
FIG. 8 is an enlarged view of section A of FIG. 7.

After forming of the helical formation 11, a polyurethane dispersion 22 is applied (see FIG. 6) to the corresponding indentation on the external side wall of the material 12 by an applicator 20. A former 21 (see FIG. 7) is then used to press the polyurethane into the material 12. However, the polyurethane 22 is not pressed by the former 21 so that it penetrates all the way through the material 12. Typically the penetration of the polyurethane 22 into the material 12 will be approximately 80% to 90% of the thickness of the material 12. In addition, the amount of polyurethane 22 applied, the shape of the former 21 and the pressure applied by the former 21 are chosen such that the polyurethane 22 overflows the external indentation of the helical formation 11. In one example, the overflow, S, is approximately 2 mm to 3 mm over the edge of the indentation (see FIG. 8).

The material 12 is then removed from the mandrel 14 and the finished article can be used as a vascular graft 30 (see FIG. 9) in the human or animal body.

FIG. 4 illustrates an alternative method of forming the helical formation 11, in which the material 12 is supported in a surrounding structure 16 together with the former 13. The surrounding structure 16 is in the form of a helical wire cage.

Although, in the example described above, heat setting is used in both the first and second settings of the material 12, any other setting method appropriate to the material may be used. For example, appropriate setting methods may include chemical, infra-red or ultra-violet setting methods, or any method that initiates or effects cross-linking in a polymer is a possibility.

However, it is desirable that, especially in the case of a vascular prosthesis, the finished product is elastically extensible, so as to be tensioned between the anastomoses. Generally, a tension resulting from a stretch of 10% of its maximum extensibility would be appropriate.

The correct helix angle of the indentation, namely the angle that gives, on theoretical, trial and error or whatever other appropriate grounds the best result in terms of the elimination of turbulent flow and dead flow areas in and downstream of the implant, the material 12 can be pre-stretched for the indentation by the 10% or other appropriate amount without significantly altering the effectiveness of the indentation.

The material 12 may be coated, after the indentation, for any reason. It may be that the material, which may, for example, be a woven or knitted polyamide or polyester, is coated with a bio-compatible material such as a polyurethane. In another example (see FIG. 5) a strand 17 may be incorporated into the indentation and sealed therein by the polyurethane dispersion 22 or by an overall coating, or a "local" coating or glue. The strand 17 may comprise a monofilament, for example, of polyester, or it may be a multifilament strand. This can help to maintain the shape and integrity of the indentation, but can also have another effect, namely that on such extension as is required to give proper implant tension, the presence of the strand will imply an undulation to the tube, mimicking natural blood vessels.

Clearly, more than one helical "start" may be applied, as by having multiple helical formers or by applying a single such former two or more times each angularly displaced for all previous applications.

While the invention has been described particularly with reference to blood flow tubing and, more particularly, with regard to implants, it is possible to provide process plant pipework with internal spiral formations by similar means. In particular, if pipework is capable of deformation, it might well be given an internal helical formation by wrapping around it a helical former and pressing the former into the pipe, e.g. by thermal contraction.

We claim:

1. A method for introducing an internal helical formation into a flexible tubular material such that the internal helical formation is capable of conferring a helical flow on liquid flowing through the tubular material, the method comprising the steps of:
   i) placing the flexible tubular material on a non-grooved mandrel, winding a thread around the material, pushing the ends of the material together so as to deform the material to have a concertinaed configuration, setting the material in that configuration, and removing the thread and the mandrel, wherein the thread is removed either before or after the material is set; and
   ii) supporting the material on a mandrel having a groove, placing a helical former corresponding to the groove around the material so as to deform the material to have an internal helical formation corresponding to the shape of the groove, setting the material in that configuration in a second setting operation, and removing the former and the mandrel.

2. A method according to claim 1, in which the material is supported in a surrounding structure together with the former.

3. A method according to claim 1 or claim 2, in which the material is thermoplastic or thermosetting and the material is set by any one of: heat setting, chemical setting, infra-red setting and ultra-violet setting.

4. A method according to claim 1, wherein the material is woven.

5. A method according to claim 1, wherein the material is knitted.

6. A method according to claim 1, in which the material is pre-tensioned during the introduction of the helical formation.

7. A method according to claim 6, in which the material is pre-tensioned to 10% of its maximum extensibility.

8. A method according to claim 1, in which a second material is applied to the material after the second setting operation.

9. A method according to claim 8, wherein the former creates an indentation in the external side wall of the material and the second material is applied to the indentation.

10. A method according to claim 9, wherein the second material overflows the indentation.

11. A method according to claim 8, wherein the second material is a polyurethane dispersion.

12. A method according to claim 8, wherein the second material is pressed into the tubular material such that the second material penetrates the tubular material.

13. A method according to claim 12, wherein the second material does not penetrate the material to the internal side wall.

14. A method according to claim 13, wherein the second material penetrates at least 50% but less than 100% into the side wall of the material.

15. A method according to claim 14, wherein the second material penetrates 80% to 90% into the side wall.

16. A method according to claim 1, in which a strand of a third material having a different modulus of elasticity to the tubular material is introduced into and secured in the helical formation after the setting operation.

17. A method according to claim 16, in which the strand material comprises a monofilament.

18. A method according to claim 16, in which the strand material comprises a multifilament strand.

19. A method according to claim 16, in which the strand is secured by applying a coating to the tubular material.

* * * * *